US009778218B2

(12) United States Patent
Barham et al.

(10) Patent No.: US 9,778,218 B2
(45) Date of Patent: Oct. 3, 2017

(54) STEAM WETNESS MEASUREMENT DEVICE

(71) Applicant: ALSTOM Technology Ltd, Baden (CH)

(72) Inventors: Scott Barham, Tamworth (GB); Ken Yves Haffner, Baden (CH); Naoki Yamada, Birr (CH); Georg Donnert, Blotzheim (FR)

(73) Assignee: General Electric Technology GmbH, Baden (CH)

( * ) Notice: Subject to any disclaimer, the term of this patent is extended or adjusted under 35 U.S.C. 154(b) by 70 days.

(21) Appl. No.: 14/807,965

(22) Filed: Jul. 24, 2015

(65) Prior Publication Data
US 2016/0047769 A1   Feb. 18, 2016

(30) Foreign Application Priority Data
Aug. 14, 2014   (EP) .................................... 14180930

(51) Int. Cl.
G01F 1/64   (2006.01)
G01N 27/22  (2006.01)
G01F 1/74   (2006.01)

(52) U.S. Cl.
CPC .............. *G01N 27/223* (2013.01); *G01F 1/64* (2013.01); *G01F 1/74* (2013.01)

(58) Field of Classification Search
CPC ...... G01N 13/00; G01N 15/082; G01N 33/74; G01N 27/223; H01L 33/502; H01L 2933/0041; G01F 1/64
USPC ....... 324/600, 500, 664, 665, 669–672, 464, 324/465, 122, 514, 76.11
See application file for complete search history.

(56) References Cited

U.S. PATENT DOCUMENTS

| 5,263,363 A | 11/1993 | Agar |
| 5,459,406 A | 10/1995 | Louge |
| 5,861,755 A * | 1/1999 | Moerk ...................... G01F 1/64 324/663 |
| 2003/0020493 A1 | 1/2003 | Haase et al. |
| 2015/0253164 A1* | 9/2015 | Kersey ...................... G01F 1/64 73/861.08 |

FOREIGN PATENT DOCUMENTS

| EP | 0407668 A1 | 1/1991 |
| GB | 2390683 A | 1/2004 |
| WO | 2011/128656 A1 | 10/2011 |

(Continued)

OTHER PUBLICATIONS

Zhenzhen Meng et al., Flowrate measurement of air-water two-phase flow using an Electrical Resistance Tomography sensor and a Venturi meter, 2009 IEEE Instrumentation and Measurement Technology Conference (I2MTC), May 5-7, 2009, Singapore, IEEE, Piscataway, NJ, USA, May 5, 2009 (May 5, 2009), pp. 118-121.

(Continued)

*Primary Examiner* — Melissa Koval
*Assistant Examiner* — Trung Nguyen
(74) *Attorney, Agent, or Firm* — GE Global Patent Operation; Cynthia W. Flanigan

(57) ABSTRACT

A method and measurement system for measuring the wetness of a gas phase of a two phase flowing fluid. The measurement system includes a container, a liquid film measurement device and an Electrical Capacitance Tomography device.

12 Claims, 1 Drawing Sheet

(56) References Cited

FOREIGN PATENT DOCUMENTS

WO    2013/063398 A2    5/2013

OTHER PUBLICATIONS

NPL—"A Novel Capacitance Sensor Principle Applicable for Spatially Resolving Downhole Measurements", IEEE Instrumentation and Measurement Technology Conference, vol. Conf. 19, May 21, 2002, pp. 1157-1160.
NPL—"Three Phase Pipe Flow Imaging Using a Capacitance Tomography System", Jan. 1, 1996, pp. 11/1-11/6.
NPL—"Measurement of Void Fraction by Using Electrical Capacitance Sensor and Differential Pressure in Air-Water Bubble Flow", Intelligent and Advanced Systems, 2012 $4^{th}$ International Conference, Jun. 12, 2012, pp. 576-581.
NPL—"Impedance Sensors for Fast Multiphase Flow Measurement and Imaging", Submitted May 5, 2008, Electrical and Computer Engineering Department at the Technische Universitat Dresden.

* cited by examiner

STEAM WETNESS MEASUREMENT DEVICE

CROSS-REFERENCE TO RELATED APPLICATIONS

This application claims priority to EP Application No. 14180930.1 filed Aug. 14, 2014, the contents of which are hereby incorporated in its entirety.

TECHNICAL FIELD

The present disclosure relates to an apparatus for measuring the wetness of a flowing gas, such as steam, in a container.

BACKGROUND INFORMATION

In power plants utilising steam, whether they be nuclear power plants, fossil fuel power plants, geothermal power plants or alternate energy power plants such as solar power plants it may be advantageous to continually measure wetness of various steam flows to enable control of steam quality thus improve process efficiency and possibly avoid, or at least minimise, component erosion.

There are a number of known techniques capable of measuring steam wetness, including tracer injection, sound measurement and Electrical Capacitance Tomography. While tracers can provide accurate measurement of wetness concentrations below 1 wt %, tracer technology does not provide continuous measurement required for control. In contrast, while measurement method based solely on Electrical Capacitance Tomography may provide continuous measurement, the method typically has limited accuracy at low wetness concentrations. The same deficiency is typically found with sound based measurement systems.

There is therefore an ongoing need to develop measurement systems that provide accurate continuous wetness measurements for steam flow streams comprising low wetness concentrations

SUMMARY

Provided is a wetness measurement device for measuring the wetness of a gas phase of a two phase flowing fluid. The measurement of the device is based on Electrical Capacitance Tomography and is capable of providing wetness measurements in the range of 0.1 wt % wetness at pressure 70 bar with an accuracy of 0.5 wt %.

The disclosure attempts to address this problem by means of the subject matters of the independent claims. Advantageous embodiments are given in the dependent claims.

One general aspect includes a measurement system for measuring wetness of gas phase of a two phase flowing fluid, such as steam. The measurement system includes a container, for containing a two phase fluiding flow and having an inner surface and an average cross sectional area, a liquid film measurement device adapted to measure a flowrate of a liquid film that forms a liquid phase of the two phase fluid through the container, an electrical capacitance tomography device having a plurality of electrodes that are located in the container and have a measurement surface, and a computer adapted to calculate wetness of a steam followed by calculating wetness of the capacitance measurements based on measurement of the Electrical Capacitance Tomography device and the calculated flowrate of a liquid film. The combination of independent flowrate and liquid film measurement instruments was found to enable reliably calculation of wetness of a gas phase in two phase flow systems using Electrical Capacitance Tomography even at low wetness.

Implementations may include one or more of the following features.

The measurement system where the flowrate of a liquid film measurement device includes a first probe, adapted to measure a gas phase void fraction in the container at the location of the first probe and a second probe, configured as part of the container and arranged downstream of and spaced apart from the first probe, and further adapted to measure a gas phase void fraction in the container at the location of the second probe.

The measurement system calculating a gas void fraction from a measurement signal from the second probe and calculating a flowrate of a liquid film by cross correlation based on the distance between the first probe and the second probe and the calculated void fraction of the first probe and the second probe.

The measurement system where the first probe and the second probe are configured as capacitance and/or conductance measuring probes.

The measurement system where the first probe and the second probe electrodes are configured as impedance measuring probes.

The measurement system where the electrical capacitance tomography device includes a plurality of electrodes with a combined measurement surface area where the combined measurement surface area is at least two times the average cross sectional area.

The measurement system where the plurality of electrodes are circumferentially distributed in the container.

The measurement system where the Electrical Capacitance Tomography device has less than twelve but greater than two electrodes.

The measurement system where the number of electrodes is precisely four. The large electrode surface size was found to significantly improved measurement accuracy enabling not only a more reliable estimate of wetness but also the ability to reduce the number of electrodes without, contrary to accepted knowledge, compromising measurement accuracy. This significantly simplifies installation of the measurement device.

The measurement system where the container includes a projection between each of the plurality of electrodes of the Electrical Capacitance Tomography device. The projections that project so as to reduce the average cross sectional area of the container.

The measurement system where the projections have a triangle shape that extends in the flow direction of the container. The projections serve the purpose of directing flowrate of a liquid film over the electrodes, which was found to provide significant improvement in the wetness calculation by preventing flow in areas of the electric field which could cause complexity of measurement.

One general aspect includes a method for measuring the wetness of two phase fluid, such as steam, flowing through a container, the method including calculating a flowrate of a liquid film that forms a liquid phase of the two phase fluid using a first measurement device and calculating wetness of the gas phase based on a measurement of an Electrical Capacitance Tomography device and the calculated flowrate of a liquid film.

It is a further object of the invention to overcome or at least ameliorate the disadvantages and shortcomings of the prior art or provide a useful alternative.

Other aspects and advantages of the present disclosure will become apparent from the following description, taken in connection with the accompanying drawings which by way of example illustrate exemplary embodiments of the present invention

BRIEF DESCRIPTION OF THE DRAWINGS

By way of example, an embodiment of the present disclosure is described more fully hereinafter with reference to the accompanying drawings, in which.

DETAILED DESCRIPTION

Figure 1:
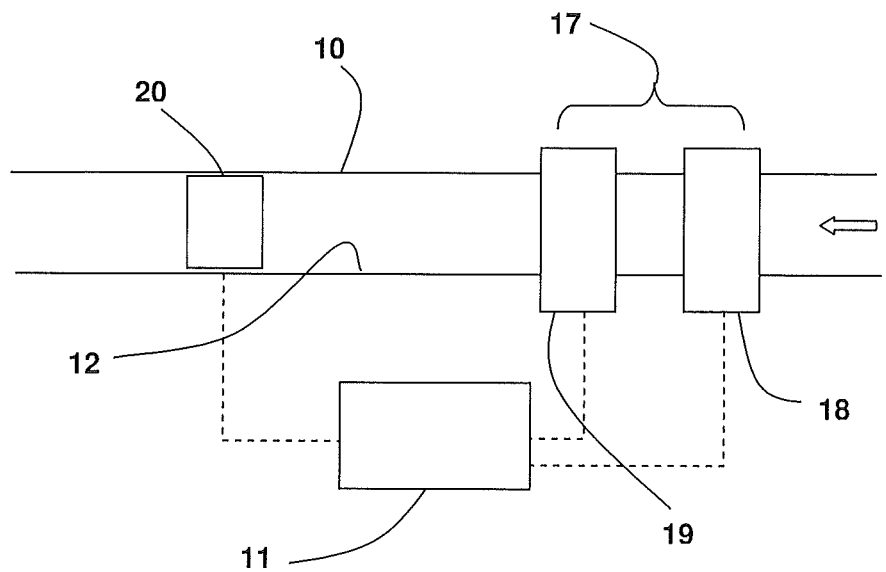
FIG. 1 is a schematic of a wetness measurement system of an exemplary embodiment of the invention.

Exemplary embodiments of the present disclosure are now described with references to the drawings, wherein like reference numerals are used to refer to like elements throughout. In the following description, for purposes of explanation, numerous specific details are set forth to provide a thorough understanding of the disclosure. However, the present disclosure may be practiced without these specific details, and is not limited to the exemplary embodiment disclosed herein.

Throughout this specification reference is made to average cross sectional area 14. This term is defined as a cross sectional limited by the inner surface of a container 10 exposed to fluids as they may flow through the container whose area is numerically averaged over the length of the container 10 in the direction of fluid flow through the container 10.

In this specification liquid film is taken to mean a thin liquid covering layer as would be understood by a person skilled in the art.

In this specification two phase flow refers to a gas/liquid flow in which a meniscus separates the two phases, wherein droplets of liquid contained in the gas phase are considered to form part of the gas phase.

In an exemplary embodiment shown in FIG. 1, an exemplary measurement system comprises a flowrate of a liquid film measurements device 17 and an Electrical Capacitance Tomography device 20, both forming part of a container 10 for containing a steam flow. The measurement system further comprises a computer 11 for calculating wetness of steam flowing through the container 10 based on measurements from the flowrate of a liquid film measurements device 17 and the Electrical Capacitance Tomography device 20. In this exemplary embodiment, the liquid film corresponds to the liquid phase of a two phase flowing fluid.

In an exemplary embodiment shown in FIG. 1 the container 10 has an inner surface 12 having an average cross sectional area 14 as well as a plurality of electrodes 22 that are located in the inner volume. Each of the electrodes 22 having a measurement surface 24.

In an exemplary embodiment shown in FIG. 1, the container 10 is a pipe segment. In a not shown embodiment, the container 10 is a duct or channel or any other container 10 whose purpose is to direct flow of a fluid between two points. In addition, along the flow length of the container 10, the cross sectional area and shape may remain constant, increase or decrease without detracting from being a container 10 of the disclosure.

In an exemplary embodiment shown in FIG. 1 the flowrate of a liquid film measurement device 17 comprises a first probe 18 and a second probe 19 located at a distance downstream of the first probe 18.

In an exemplary embodiment, by means of either capacitance, conductance or impedance each of the first probe 18 and second probe 19 measure a gas void fraction of the container 14 at the location of each of the first probe 18 and the second probe 19. By cross correlation of the void fractions estimated by the first probe 18 and the second probe 19, and further consideration of a known distance between the first probe 18 and the second probe 19, a computer 11 calculates the flow rate of a film in the container 10 using known cross correlation methods. The computer further uses the flow rate of the fluid, which may be either mass of volumetric flow rate, to correct the measurement signal from the Electrical Capacitance Tomography device 20 so as to provide an estimate of gas phase wetness.

Figure 2:
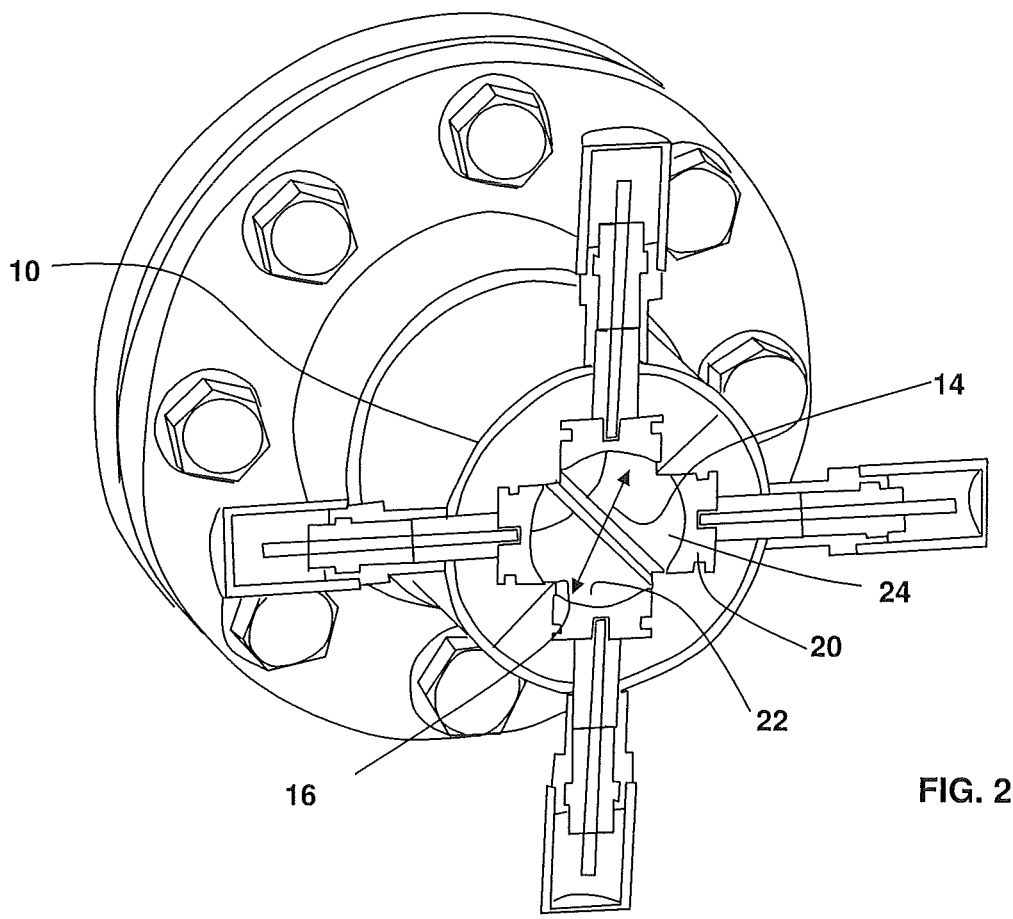
FIG. 2 is a cut view of an Electrical Capacitance Tomography device of FIG. 1.

In an exemplary embodiment shown in FIG. 2, the Electrical Capacitance Tomography device 20 is contained with a container 10. A plurality of electrodes 22 are located in the container 10 and form part of the inner surface 12 of the container 10 of the measurement system so as to be circumferentially distributed in the container 10

In an exemplary embodiment shown in FIG. 1 the Electrical Capacitance Tomography device 20 is located downstream of the flowrate of a liquid film measurement device 17.

In a not shown exemplary embodiment, the Electrical Capacitance Tomography device 20 is located upstream of the flowrate of a liquid film measurement device 17.

In a not shown exemplary embodiment, the electrodes 22 are contained inside the container 10 but do not form part of the inner surface 12 of the container 10. In such an arrangement, the electrodes 22 are located in the flow path between inner walls that form inner surfaces 12 of the container 10.

The electrodes additionally contain a measurement surface 24 exposed to fluid flowing in the container 10 in the normal flow direction. The area of the measurement surface 24 is therefore the area of the electrode 22 that is exposed to flowing gas and configured to measure a characteristic of the fluid. In an exemplary embodiment were the electrodes 22 are adapted for use as Electrical Capacitance Tomography measurement sensors the measured characteristic is permittivity.

In an exemplary embodiment, the ratio of the area of the combined measurement surface 24 of the plurality of electrodes 22 to average cross sectional area 14 of the container 10 is greater than two. For example, if the average cross sectional area 14 of the container is 10 cm, the surface area of the plurality of electrodes 22 would be at least 20 cm$^2$. While, from a measurement point of view there is no upper limit to the size of the plurality of electrodes 22, from a practical point of view, in consideration of the reduced measurement benefit of increasing the size of the plurality of electrodes significantly above two, the area of the plurality of electrodes 22 may be limited to six, preferably four, times the average cross sectional area 14 of the container.

In an exemplary embodiment shown in FIG. 2, the number of electrodes of the Electrical capacitance Tomography device is preferably between two and twelve and more preferably precisely four.

In an exemplary embodiment shown in FIG. 2, the inner surface 12 of the container 10 comprises projections 16 that extend between the electrodes 22 of the Electrical Capacitance Tomography device 20. The purpose of the projections 16 is to ensure flowrate of a liquid film passes over the electrodes 22 rather that around the electrodes 22. To achieve this purpose, in an exemplary embodiment shown in FIG. 2, the projections 16 have a triangle shape that extends in the flow direction of the container 10. The projections 16 may, however, take other forms and shape that achieves the purpose of the projections 16.

Although the disclosure has been herein shown and described in what is conceived to be the most practical exemplary embodiment, the present disclosure can be embodied in other specific forms. The presently disclosed embodiment is considered in all respects to be illustrative and not restricted. The scope of the disclosure is indicated by the appended claims rather that the foregoing description and all changes that come within the meaning and range and equivalences thereof are intended to be embraced therein.

The invention claimed is:

1. A measurement system for measuring wetness of a flowing fluid having a gas phase and a liquid phase, the measurement system comprising:
   a container, for containing the fluid, having an inner surface and an average cross sectional area;
   a flowrate measurement device adapted to measure a flowrate of the liquid film formed on the inner surface;
   an Electrical Capacitance Tomography device, for measuring permittivity of the flowing fluid, having a plurality of electrodes, located in the container, wherein the plurality of electrodes are arranged together to define a combined measurement area; and
   a computer adapted to:
      calculate the flowrate of the liquid film in the container; and then
   calculate wetness of the gas phase based on a measurement of the Electrical Capacitance Tomography device and the calculated the flowrate of the liquid film.

2. The measurement system of claim 1 wherein the flowrate measurement device comprises:
   a first probe, adapted to measure a gas phase void fraction in the container at the location of the first probe; and
   a second probe, configured as part of the container and arranged downstream of and spaced apart from the first probe by a distance, adapted to measure a gas void fraction in the container at the location of the second probe, wherein the computer is adapted to calculate the wetness being configured to:
   calculate the gas void fraction from the first probe;
   calculate the gas void fraction from the second probe; and
   calculate the flowrate of the liquid film by cross correlation based on the distance between the first probe and the second probe and the calculated gas void fraction of the first probe and the second probe.

3. The measurement system of claim 2 wherein the first probe and the second probe are configured as capacitance and/or conductance measuring probes.

4. The measurement system of claim 2 wherein the first probe and the second probe electrodes are configured as impedance measuring probes.

5. The measurement system of claim 1 wherein the combined measurement surface area is at least two times the average cross sectional area.

6. The measurement system of claim 1 wherein the electrodes of the Electrical Capacitance Tomography device are circumferentially distributed in the container.

7. The measurement system of claim 1 wherein the Electrical Capacitance Tomography device has less than twelve but greater than two electrodes.

8. The measurement system of claim 1 wherein the Electrical Capacitance Tomography device has precisely four electrodes.

9. The measurement system of claim 1 wherein the container comprises at least one projection, between each of the plurality of electrodes of the Electrical Capacitance Tomography device, configured to reduce the average cross sectional area.

10. The measurement system of claim 9 wherein the projections have a triangle shape that extends in a flow direction of the container.

11. A method for measuring a wetness of fluid having a gas phase and a liquid phase, flowing through a container, the method comprising:
    calculating a flowrate of a liquid film that forms the liquid phase based on a measurement of a flowrate measurement device; and
    calculating a wetness of the gas phase based on a measurement of an Electrical Capacitance Tomography device and the calculated flowrate of a liquid film.

12. The method of claim 11 wherein the calculating the flowrate of the liquid film comprises:
    calculating a gas void fraction in the container using a first probe configured as either a capacitance or conductance measuring probe;
    calculating a gas void fraction in the container using a second probe, configured as either a capacitance or conductance measuring probe, located at a first distance downstream of the first probe; and
    calculating the flowrate of the liquid film by cross correlation based on the first distance between the first probe and the second probe and the calculated gas void fraction of the first probe and the calculated gas void of the second probe.

* * * * *